United States Patent
Delija

(10) Patent No.: US 9,486,370 B2
(45) Date of Patent: Nov. 8, 2016

(54) MEN'S BRIEFS WITH SEPARATE SPACE FOR PENIS COMPRISING ABSORBENT RECEPTACLE

(76) Inventor: Frane Delija, Split (HR)

( * ) Notice: Subject to any disclaimer, the term of this patent is extended or adjusted under 35 U.S.C. 154(b) by 0 days.

(21) Appl. No.: 14/407,080

(22) PCT Filed: Jun. 12, 2012

(86) PCT No.: PCT/HR2012/000014
§ 371 (c)(1),
(2), (4) Date: Dec. 11, 2014

(87) PCT Pub. No.: WO2013/186577
PCT Pub. Date: Dec. 19, 2013

(65) Prior Publication Data
US 2015/0173974 A1 Jun. 25, 2015

(51) Int. Cl.
| | |
|---|---|
| *A61F 13/66* | (2006.01) |
| *A61F 13/505* | (2006.01) |
| *A61F 13/491* | (2006.01) |
| *A41B 9/02* | (2006.01) |
| *A61F 13/471* | (2006.01) |

(Continued)

(52) U.S. Cl.
CPC ............. *A61F 13/505* (2013.01); *A41B 9/004* (2013.01); *A41B 9/023* (2013.01); *A61F 13/471* (2013.01); *A61F 13/4906* (2013.01); *A61F 13/4915* (2013.01); *A61F 13/49017* (2013.01); *A61F 13/66* (2013.01); *A61F 13/15268* (2013.01); *A61F 13/49006* (2013.01); *A61F 2013/5055* (2013.01)

(58) Field of Classification Search
CPC ........... A61F 13/15268; A61F 13/471; A61F 13/49006; A61F 13/4915; A61F 13/505; A61F 13/66; A61F 13/68; A61F 13/72; A61F 2013/15276; A61F 2013/5055; A41B 9/004; A41B 9/023
USPC ......................................... 604/349, 535, 534
See application file for complete search history.

(56) References Cited

U.S. PATENT DOCUMENTS

| | | | |
|---|---|---|---|
| 4,695,279 A * | 9/1987 | Steer | A61F 5/4401 2/406 |
| 5,275,592 A | 1/1994 | Grizzaffi | |

(Continued)

FOREIGN PATENT DOCUMENTS

| | | |
|---|---|---|
| GB | 2174288 A | 11/1986 |
| WO | 8605387 A1 | 9/1986 |

(Continued)

*Primary Examiner* — Lynne Anderson
(74) *Attorney, Agent, or Firm* — St Onge Steward Johnston and Reens LLC

(57) ABSTRACT

Men's briefs with separated space for penis has a flexible belt, panel, front outer insert and front inner insert, forming a separated space for a penis between the front outer insert and front inner insert. The front inner insert is formed from two overlapping sewed parts and having curved hems forming a circular adjustable orifice for inserting the penis into the separated space. The orifice encircles the penis and prevents it from falling out from separated space. The briefs are further provided with removable incontinence receptacle having an orifice, which is placed within front outer insert and front inner insert through an opening. The incontinence receptacle has the same shape and dimensions as the inserts so that the incontinence receptacle orifice aligns with the circular adjustable orifice of the inserts so that the incontinence receptacle receives the penis.

20 Claims, 5 Drawing Sheets

Figure 1:
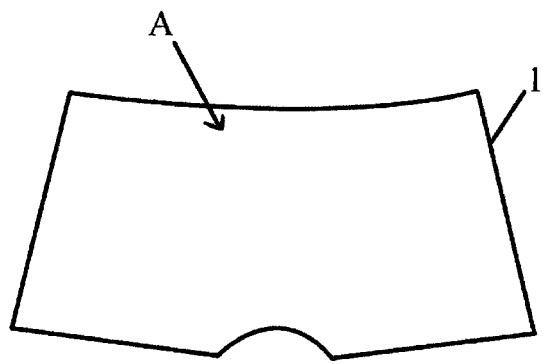

(51) Int. Cl.
*A41B 9/00* (2006.01)
*A61F 13/49* (2006.01)
*A61F 13/15* (2006.01)

(56) References Cited

U.S. PATENT DOCUMENTS

| 5,618,279 | A | * | 4/1997 | Pudlo | A61F 5/40 |
| | | | | | 2/403 |
| 5,649,913 | A | * | 7/1997 | Cohen | A61F 5/449 |
| | | | | | 2/401 |
| 5,669,902 | A | * | 9/1997 | Sivilich | A61F 5/4401 |
| | | | | | 604/385.14 |
| 5,707,364 | A | | 1/1998 | Coates | |
| 5,722,127 | A | | 3/1998 | Coates | |
| 6,569,135 | B1 | | 5/2003 | Mula | |
| 6,817,992 | B1 | * | 11/2004 | Sassak | A61F 5/453 |
| | | | | | 604/349 |
| 2005/0015067 | A1 | | 1/2005 | Suzuki et al. | |
| 2005/0033258 | A1 | | 2/2005 | Suzuki et al. | |
| 2006/0276764 | A1 | | 12/2006 | Warne | |
| 2011/0077610 | A1 | | 3/2011 | Kikumoto et al. | |

FOREIGN PATENT DOCUMENTS

| WO | 8806008 | A1 | 8/1988 |
| WO | 8900037 | A1 | 1/1989 |
| WO | 2012013991 | A1 | 2/2012 |

* cited by examiner

MEN'S BRIEFS WITH SEPARATE SPACE FOR PENIS COMPRISING ABSORBENT RECEPTACLE

TECHNICAL FIELD

The present invention relates to men's underwear, in particular men's underpants having separate space to physically separate the penis from the testicles at the inner side of their front part, and having a removable incontinence absorbent receptacle.

TECHNICAL PROBLEM AND BACKGROUND ART

The penis and the testicles are constantly in contact, which is not good from the hygienic and health points of view. Due to their position, these organs are constantly exposed to sweating. Particularly negative effect is from the drops of urine remaining after urination or caused by problems with mild incontinence.

The present invention aims to provide versatile men's briefs especially suitable for wear by active persons who suffer from mild urinary incontinence or for patients recovering after surgery. Moreover, it is an advantage of the arrangements disclosed herein that the briefs are intended for those not incontinent and for those suffering incontinence.

The technical problem that is solved by this invention relates to designing of men's briefs, where the penis will be physically separated from the testicles, and having a removable incontinence absorbent receptacle adapted to fit within said men's briefs in an easy and comfortable way with tightening means for preventing the penis from going beyond the incontinence absorbent receptacle.

Since the penis is naturally slightly directed to the left or right side, the present invention provides such natural position avoiding any pressure caused by briefs. An overlapping inner insert prevents the penis from falling out of the briefs' separate space, especially when the wearer is in a sitting position for an extended period of time. A further advantage of the present invention is that the briefs' orifice is oriented left or right, depending on the customer's preferences.

A further advantage of the present invention is that the briefs adjustable tightening around the penis prevents the penis from going beyond the incontinence absorbent receptacle during sleep or any other sport activity.

Document GB 2174288 A is closest prior art and discloses a pair of men's briefs (200), which include a pocket located in the crotch region (212) and defined by an outer wall of a liquid-impermeable material which is longer than it is wide and an inner wall of like material which has a central hole therein, and the outer and inner walls are positioned so as to retain, in use, an elongate absorbent pad in the pocket. The present invention differs from the technology disclosed in document GB 2174288 A in that the opening in the present invention's briefs has a circular like form which encircles penis in a way that prevents its falling out from separated space, and furthermore the present invention's briefs utilize an elastic means for adjustably tightening the briefs around the penis. Another advantage over document GB 2174288 A relates to the material of the briefs and form of the incontinence absorbent receptacle. According to document GB 2174288 A, the absorbent pad is in elongated form and the crotch region of the briefs is made of liquid-impermeable material.

According to the present invention parts of the briefs are not made of a liquid-impermeable material. Instead, the absorbent article is in the form of a receptacle; it can be disposable or washable and comfortably fits within briefs. Further, since the receptacle according to present invention is in the form of a three dimensional container, it ensures retention of the urine within the receptacle and prevents urine from contacting and wetting the briefs.

The men's briefs with separate space for the penis adapted for incorporating a removable incontinence absorbent receptacle according to the present invention makes for a very useful underwear for improving men's health, that can be manufactured very economically and in numerous embodiments. It includes essential improvements relative to previously known briefs and incontinence absorbents of this type.

DETAILED DESCRIPTION OF THE INVENTION

The essence of the invention is men's briefs with a separate space for a penis placed at the inner side of their front part and including a removable incontinence absorbent receptacle which is adjustably placed within the separate space for penis.

The men's briefs with separated space for the penis comprises a removable incontinence absorbent receptacle, made as short or long leg briefs, with a flexible belt, panel, front outer insert and front inner insert, wherein separated space for the penis is formed by the front outer insert and front inner insert; said inserts are connectable to the panel and optional part in a manner to form men's briefs, wherein the front inner insert has shape and dimensions substantially the same as the front outer insert. The front inner insert is formed from two overlapping sewed parts having curved hems, where the curved hems form a circular like adjustable orifice for inserting the penis into a separated space. The adjustable orifice is placed in the briefs midline, and said orifice encircle the penis in a way that prevents its falling out from the separated space. The adjustable orifice is placed in the briefs' center line and is oriented on the left or right side by rotating the front inner insert by 180° around the briefs midline. Additionally, the curved hems have an elastic means for adjustably encircling the penis, where, according to one embodiment of present invention, said elastic means can be tightened by the means on the outer side of the briefs. The shape of the opening for entering the penis and the height at which it is made are adjusted to allow the penis to smoothly enter its separate space when the briefs are being put on. This way, the testicles remain in their normal position, always physically separated from the penis. The men's briefs are further provided with a removable incontinence receptacle having an orifice for receiving the penis, where the incontinence receptacle is placed within the front outer insert and the front inner insert, whereat the incontinence receptacle has a shape substantially the same as said inserts and has dimensions to fit within said inserts. According to the one embodiment of the present invention, the removable incontinence receptacle is disposable. According to another embodiment of the present invention, the removable incontinence receptacle is washable and can be reused.

DETAILED DESCRIPTION OF DRAWINGS

Figure 2:
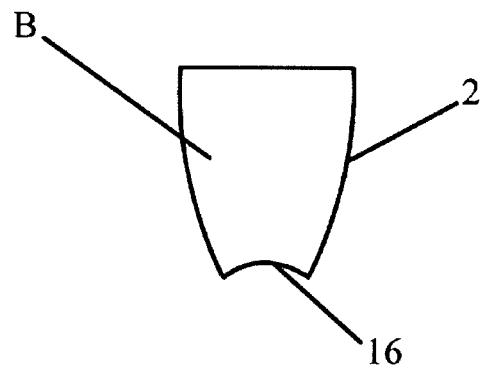
Figure 3:
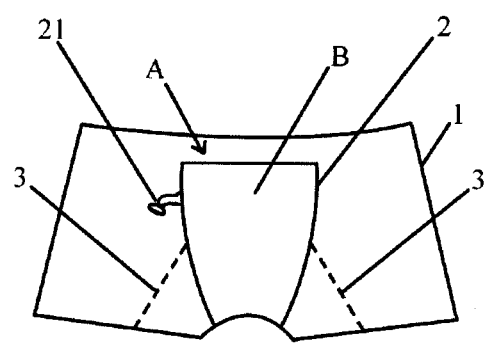
Figure 4:
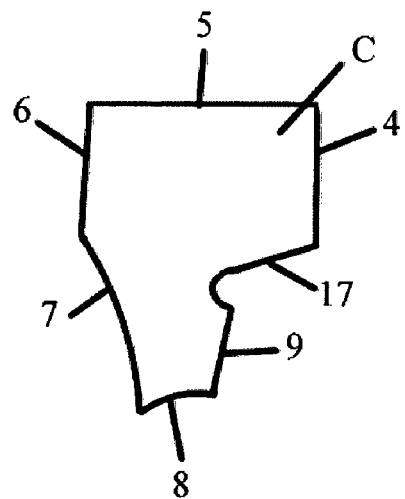
Figure 5:
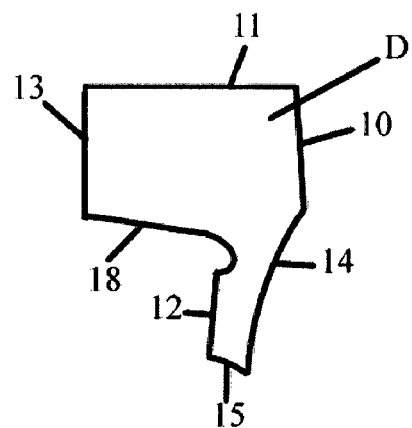
Figure 5B:
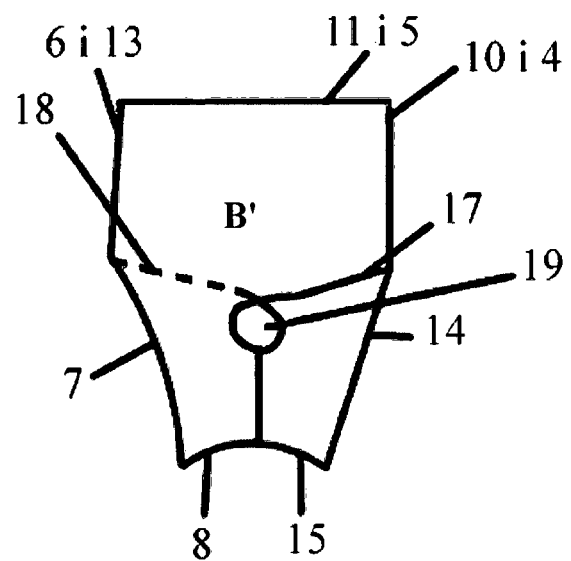
Figure 5A:
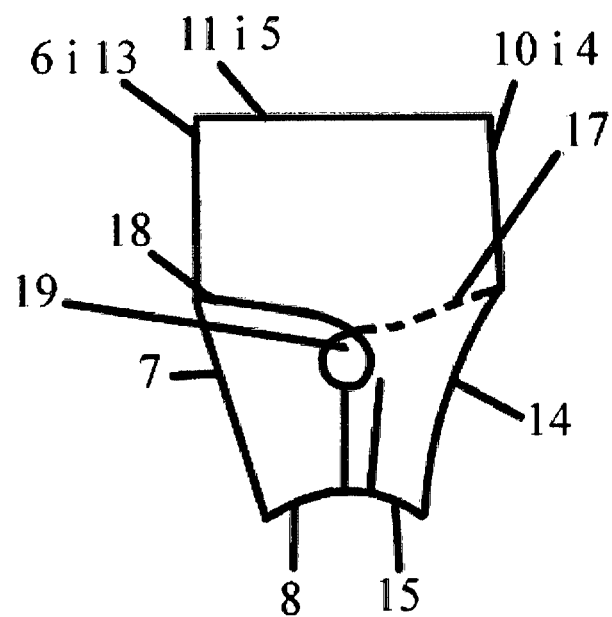
Figure 6A:
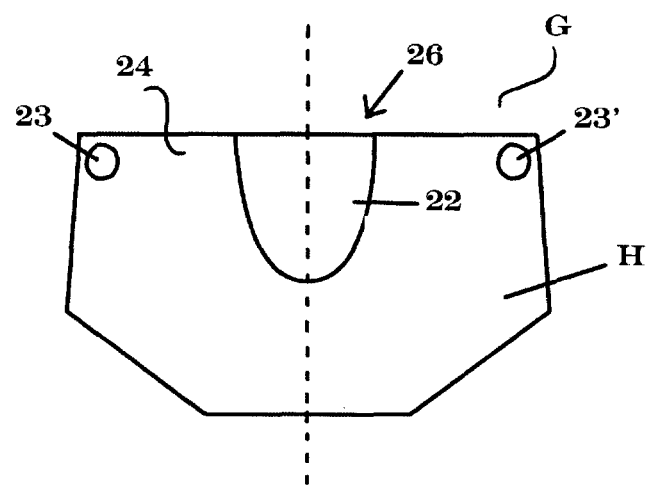
Figure 6B:
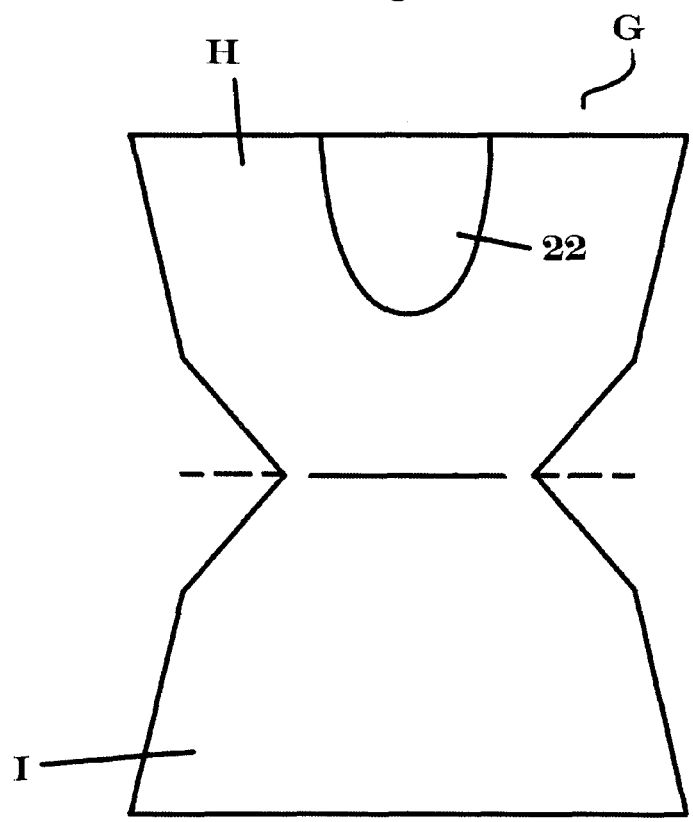
Figure 7A:
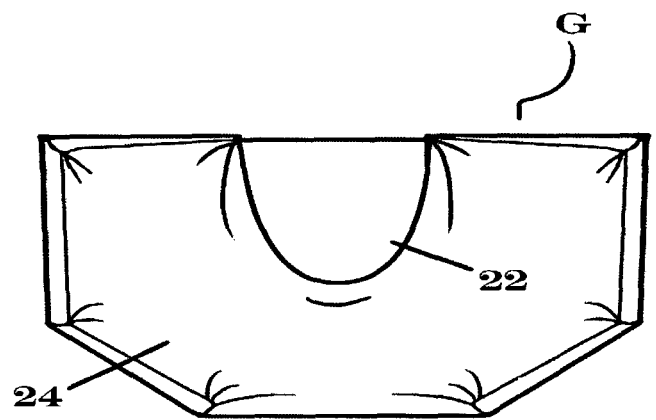
Figure 7B:
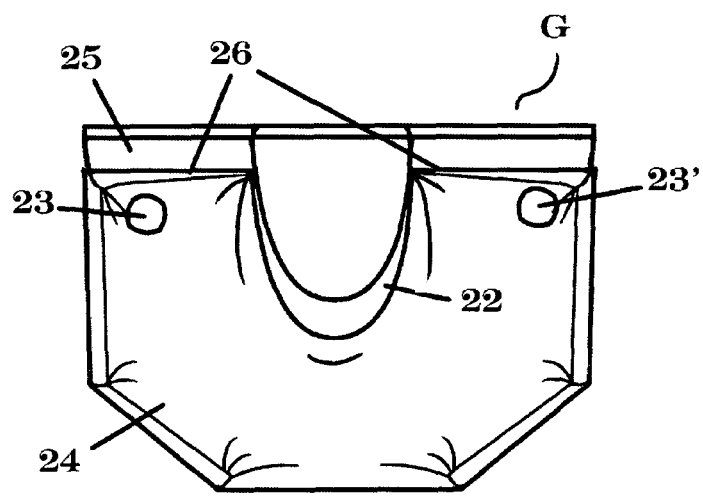

Invention will be below described in detail with reference to drawings where:

FIG. 1. shows the back and side panel A of the briefs,

FIG. 2. shows the front outer insert B,

FIG. 3. shows the outer front view of the briefs,

FIG. 4. shows view of the part C of the inner panel,

FIG. 5. shows view of the part D of the inner panel,

FIGS. 5a. and 5b show view of the front inner insert B' with orifice 19 left or right oriented, FIG. 6a. schematically shows incontinence receptacle (G) with orifice 22, FIG. 6b. schematically shows dismantled incontinence receptacle (G) with orifice 22, FIG. 7a shows front side of the removable incontinence receptacle with U-shaped orifice, and FIG. 7b schematically shows the outer liquid barrier cover and placing inner absorption receptacle within it.

FIGS. 1 to 5b show an embodiment of men's briefs with a separated space for penis, made as short or long as the leg of the briefs, with a flexible belt, a panel (A), a front outer insert (B) and a front inner insert (B'), wherein the separated space for the penis is formed by the front outer insert (B) and the front inner insert (B'); the inserts (B) and (B') are connected to the panel (A) and an optional part (3) in a manner to form men's briefs, wherein the front inner insert (B') has a shape and dimensions substantially the same as the front outer insert (B). The front inner insert (B') is formed from two overlapping sewed parts (C) and (D) having curved hem 17 and curved hem 18, respectively, where curved hems 17 and 18 form a circular like adjustable orifice 19 for inserting the penis into the separated space. As illustrated on FIGS. 5a and 5b, according to the embodiment of the invention, it is provided that part (C) overlaps part (D) or part (D) overlaps part (C), without any further modification of said parts (C) and (D) and other parts of briefs. FIGS. 5a and 5b illustrate adjustable orifice (19) placed in the briefs' center line. Orifice 19 encircles the penis in a way that prevents its falling out from the separated space and its facilitates stable positioning. By rotating front inner insert (B') by 180° around the briefs midline, adjustable orifice (19) can be left or right side oriented thus enabling more comfortable placing of penis on the left or right side according to the user's preferences. Additionally hems 17 and 18 have an elastic means for adjustably encircling the penis, where, according to one embodiment of the present invention, said elastic means can be tightened by the drawstring (21).

As shown on FIGS. 4 and 5, front inner insert (B') is formed from two parts (C) and (D) with mutually sewed hems 6 and 13, 8 and 15, 9 and 12, where curved hems 17 and 18 form a circular like adjustable orifice 19 for inserting the penis into the separated space, where orifice (19) is placed in the briefs midline, wherein orifice 19 encircles the penis in a way that prevents its falling out from the separated space. With reference to the FIGS. 5a and 5b, front inner insert (B') being sewed to the inner side of the outer panel (A) and front outer insert (B) at least through hem (7) and hem (14), and through sewing hem (8) and hem (15) to hem (16). Furthermore, inserts B and B' are connected to the outer panel (A) through hems (6 and 13), (10 and 4) and (8 and 15). Outer panel (A) constitutes the back, side and partially front side of the briefs. Outer panel (A) can be tailored in one piece where that one piece includes part of the front panel (3). For a person skilled in the art, it is obvious that certain modifications of the design of the outer panel (A) and inserts (B, B') are possible without impact on the scope of the invention. For instance, outer panel A can be tailored from more than one piece of fabric (e.g. part (3) can be a separate part of the briefs).

With reference to FIGS. 6a to 7b, the men's briefs are further provided with a removable incontinence receptacle (G) having an orifice (22). Incontinence receptacle (G) is placed within the front outer insert (B) and the front inner insert (B') thru an opening formed between hems (11, 5). The incontinence receptacle (G) has a shape substantially the same as inserts (B, B') and has dimensions to fit within inserts (B, B') in a manner so that the orifice (22) lines up with the orifice (19) such that the penis may pass thru orifices (22, 19) and rest within the incontinence receptacle (G). The expression "dimensions to fit within", and other variants of said expression, in the present application mean that the dimensions of an element to which said expression relates are such that it can be inserted or positioned within a defined space and can not be displaced from its position after insertion. The best mode of carrying out the invention is for the incontinence receptacle (G) to have the same shape as inserts (B, B') and dimensions to fit within inserts (B, B'), and for the orifice (22) to be lined up with the orifice (19). The hems (17) and (18) have elastic means for adjustably encircling the penis and additionally the elastic means can be tightened by the means (21). These features retain the penis within the incontinence absorbent receptacle during sleep or intense activities.

As shown on the FIGS. 7a, 7b the incontinence receptacle (G) consists of the outer liquid barrier cover (24), and the inner absorption receptacle (25) having substantially the same shape as the cover (24) and dimensions to fit within the cover (24). Both the cover (24) and receptacle (25) are provided with matching orifices at the same location such that, when combined to form the incontinence receptacle (G), the orifice (22) is formed. The orifice (22) can be circular or U-shaped or of any other shape suitable for receiving the penis. The orifice (22) is placed in the center line of the incontinence receptacle (G). The incontinence receptacle (G) is defined by a receptacle front panel (H) and a receptacle back panel (I) shown in FIG. 6b. Panels (H) and (I) are on the edges mutually firmly connected. In another embodiment, the upper end of cover (24) is provided with an opening (26) for inserting the inner absorption receptacle (25). The inner absorption receptacle (25) is defined by two planes mutually firmly connected on their edges forming a pocket like receptacle.

According to one embodiment of the invention, the incontinence receptacle (G) is disposable and consists of the outer liquid barrier cover (24) and inner absorption receptacle (25) which cover (24) and receptacle (25) are on their edges mutually firmly connected. In this embodiment, the cover (24) is not provided with opening (26). In another embodiment of the invention, the incontinence receptacle (G) is not disposable where cover (24) and inner absorption receptacle (25) are not mutually firmly connected thus enabling changing and/or washing of the absorption receptacle (25). In order to fix incontinence receptacle (G) within inserts (B, B'), they are provided with detachable means (23, 23'). Using means (23, 23'), the incontinence receptacle (G) is detachably connected to the front inner insert (B') and/or front outer insert (B).

The men's briefs with a separate space for the penis comprising a removable incontinence absorbent receptacle, according to this invention, eliminates deficiencies of the commonly sold men's briefs, including their hygienic and health properties and physical discomforts. The separate space for the penis is situated at the inner side of the front part of the briefs, between the front outer insert and front inner insert. The removable incontinence absorbent is adjustably placed within the separate space for the penis. Regardless of the body movements and position, the penis will always remain in the separate space containing the incontinence absorbent, which fully satisfies the essence and the function of the invention.

REFERENCE SIGNS

The reference signs used in the description and figures have the following meaning:
A—back and side panel of briefs
B—front outer insert
B'—front inner insert
C—part of the inner panel
D—part of the inner panel
G—incontinence receptacle
H—receptacle front panel
I—receptacle back panel
1—panel A hem
2—insert B hem
3—optional part of the front panel
4—hem sewed to hem 10
5—hem 6—hem sewed to hem 13
7—sewed to inner side of the outer panel
8—hem sewed to hem 16
9—hem sewed to hem 12
10—hem sewed to hem 4
11—hem
12—hem sewed to hem 9
13—hem sewed to hem 6
14—hem sewed to hem inner side of the outer panel
15—hem sewed to hem 16
16—hem sewed with hems 8 and 15
17—curved hem
18—curved hem
19—opening
20—seam
21—means suitable for adjustment of opening 19
22—orifice
23, 23'—detachable means
24—outer impermeable cover-outer liquid barrier cover
25—inner absorption receptacle
26—opening Persons skilled in the art will find it obvious that certain modifications of the design of the separate penis space are possible and accordingly of the removable incontinence absorbent receptacle, given the briefs design, however not leaving the spirit of the invention.

The invention claimed is:

1. Men's briefs with a separated space for receiving the penis comprising:
   a removable incontinence absorbent receptacle, a flexible belt, a panel, a front outer insert, and a front inner insert, wherein the separated space is formed by the front outer insert and the front inner insert;
   the front outer and front inner inserts being connectable to the panel, wherein the front inner insert has a shape and dimensions substantially the same as the front outer insert;
   the front inner insert being formed from a first overlapping sewed part and a second overlapping sewed part, each comprising a curved elastic hem and a top hem, wherein the curved hem of the first overlapping sewed part and the curved hem of the second overlapping sewed part form a substantially circular adjustable elastic orifice for inserting the penis into the separated space, the adjustable orifice encircling the penis to retain the penis in the separated space;
   the removable incontinence receptacle comprising first and second planes that are mutually firmly connected on their edges, the first plane comprising an orifice, the incontinence receptacle being removeably arrangeable within the separated space formed by the front outer insert and the front inner insert through an aperture located between the top hems of the first and second overlapping sewed parts, the incontinence receptacle having a shape substantially the same as the front outer and front inner inserts and dimensions to fit within the front outer and front inner inserts;
   wherein the orifice of the incontinence receptacle and the adjustable orifice of the front inner insert are aligned to receive the penis within the incontinence receptacle when the incontinence receptacle is arranged within the separated space of the men's briefs.

2. The men's briefs according to claim 1, wherein the incontinence receptacle further comprises an outer liquid barrier cover and an inner absorption receptacle, each comprising an orifice that aligns with the adjustable orifice of the front inner insert to receive the penis within the incontinence receptacle when the incontinence receptacle is arranged within the separated space of the men's briefs.

3. The men's briefs according to claim 2, wherein the inner absorption receptacle is disposable or washable, and wherein the cover comprises an opening.

4. The men's briefs according to claim 2, wherein the incontinence receptacle is disposable and the inner absorption receptacle and outer liquid barrier cover are mutually firmly connected on their edges and the orifice of the inner absorption receptacle lines up with the orifice of the outer liquid barrier cover.

5. The men's briefs according to claim 1, wherein the orifice of the incontinence receptacle is circular, U-shaped, or of any other shape suitable for receiving the penis.

6. The men's briefs according to claim 1, wherein the orifice of the incontinence receptacle is located on the incontinence receptacle's center line.

7. The men's briefs according to claim 1, wherein the adjustable orifice of the front inner insert is located on the briefs' center line.

8. The men's briefs according to claim 1, wherein the curved hems of the first and second overlapping sewed parts comprise elastic means for adjustably encircling the penis.

9. The men's briefs according to claim 8, further comprising a drawstring for tightening the elastic means of the curved hems of the first and second overlapping sewed parts.

10. The men's briefs according to claim 1, wherein the incontinence receptacle further comprises detachable means suitable for fastening the incontinence receptacle to one or both of the front inner insert and the front outer insert.

11. An incontinence receptacle comprising first and second planes, the first and second planes being mutually firmly connected, the first plane comprising an orifice, the incontinence receptacle being removeably arrangeable within men's briefs such that the orifice is located to receive the wearer's penis within the incontinence receptacle.

12. The incontinence receptacle according to claim 11, further comprising an inner absorption receptacle and an outer liquid barrier cover, the inner absorption receptacle being disposable or washable, and the outer liquid barrier cover comprising an opening.

13. The incontinence receptacle according to claim 11, wherein the incontinence receptacle is disposable and comprises an outer liquid barrier cover and an inner absorption receptacle each comprising an orifice adapted to receive the wearer's penis within the incontinence receptacle, the outer liquid barrier cover and the inner absorption receptacle being mutually firmly connected on their edges.

14. The incontinence receptacle according to claim 13, wherein the orifice of the incontinence receptacle is circular, U-shaped, or of any other shapes suitable for receiving the penis.

15. The incontinence receptacle according to claim 14, wherein the orifice of the incontinence receptacle is located on the incontinence receptacle's center line.

16. The incontinence receptacle according to claim 15, further comprising detachable means suitable for fastening the incontinence receptacle to the men's briefs.

17. A pair of men's underwear comprising:
   a panel, a front outer insert, and a front inner insert, and a removable incontinence receptacle;
   the front outer insert and the front inner insert having a substantially similar shape and being connected to the panel to create a separated space having a front space for receiving the wearer's penis and a rear space;
   the front inner insert comprising first and second overlapping sewn parts each comprising a curved hem, wherein the curved hems form a substantially circular elastic orifice through which the wearer's penis may be inserted into the front space, the orifice encircling and retaining the wearer's penis;
   the removable incontinence receptacle having a shape and dimensions to fit within the front space, and being positionable within the front space through an opening between an upper hem of the front inner insert and an upper hem of the front outer insert;
   the removable incontinence receptacle being formed from a first plane and a second plane joined along peripheral edges of the first and second planes, the first plane having an orifice aligned with the orifice of the front inner insert to receive the wearer's penis within the incontinence receptacle when the incontinence receptacle is arranged within the front space.

18. The men's underwear according to claim 17, wherein the removable incontinence receptacle further comprises an outer liquid barrier cover and an inner absorption receptacle, the inner absorption receptacle comprising an orifice adapted to align with the adjustable orifice of the front inner insert to receive the wearer's penis within the removable incontinence receptacle when the removable incontinence receptacle is arranged within the separated space.

19. The men's underwear according to claim 17, wherein the curved hems of the first and second overlapping sewed parts are elastic hems.

20. The men's underwear according to claim 17, wherein the removable incontinence receptacle is detachably fastened to the men's underwear.

* * * * *